(12) United States Patent
Tzeng et al.

(10) Patent No.: US 8,138,184 B2
(45) Date of Patent: Mar. 20, 2012

(54) ISOXAZOLE DERIVATIVES AND PHARMACEUTICAL COMPOSITIONS COMPRISING THE SAME

(75) Inventors: Cherng-Chyi Tzeng, Kaohsiung (TW); Yeh-Long Chen, Kaohsiung (TW); Gwo-Jaw Wang, Kaohsiung (TW); Mei-Ling Ho, Kaohsiung (TW); Je-Ken Chang, Kaohsiung (TW); Yin-Chih Fu, Kaosiung (TW)

(73) Assignee: Kaohsiung Medical University, Kaohsiung (TW)

( * ) Notice: Subject to any disclaimer, the term of this patent is extended or adjusted under 35 U.S.C. 154(b) by 269 days.

(21) Appl. No.: 12/243,376

(22) Filed: Oct. 1, 2008

(65) Prior Publication Data
US 2009/0215768 A1 Aug. 27, 2009

(30) Foreign Application Priority Data
Feb. 26, 2008 (TW) .............................. 97106587 A

(51) Int. Cl.
*A61K 31/5377* (2006.01)
*A61K 31/4525* (2006.01)
*A61K 31/42* (2006.01)
*C07D 413/02* (2006.01)
*C07D 413/12* (2006.01)
*C07D 261/06* (2006.01)

(52) U.S. Cl. ............... 514/236.8; 514/326; 514/378; 544/137; 546/209; 548/247

(58) Field of Classification Search ............... 514/233.5, 514/254.11, 378; 544/151; 548/247
See application file for complete search history.

(56) References Cited

U.S. PATENT DOCUMENTS

| 5,247,102 A | 9/1993 | Kallay et al. |
| 5,859,257 A | 1/1999 | Talley |

FOREIGN PATENT DOCUMENTS

| EP | 0136569 A2 | 9/1984 |
| EP | 0941992 A1 | 9/1999 |
| EP | 0941992 B1 | 5/2002 |
| JP | 09-268187 | 10/1997 |
| JP | 11-012265 | 1/1999 |
| WO | WO 91/15483 | 10/1991 |

OTHER PUBLICATIONS

Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Bondarenko et al., Reaction of Natural Isoflavonoids and Their Analogs with Hydroxylamine, 2007, Chemistry of Natural Compounds, vol. 43, No. 4, 402-407.*
Habeeb et al., "Design and Synthesis of 4,5-Diphenyl-4-isoxazolines: Novel Inhibitors of Cyclooxygenase-2 with Analgesic and Antiinflammatory Activity,"J. Med Chem, 2001, pp. 2921-2927, vol. 44.
Habeeb et al., "Design and Syntheses of Diarylisoxazoles: Novel Inhibitors of Cyclooxygenase-2 (COX-2) With Analgesic-Antiinflammatory Activity," Drug Development Research, 2000, pp. 273-286, vol. 51.
Zhang et al., "Highly Potent Triazole-Based Tubulin Polymerization Inhibitors," J. Med. Chem, 2007, pp. 749-754, vol. 50.
Sun et al., "Synthesis and cytotoxic activities of 4,5-diarylisoxazoles," Bioorganic and Medicinal Chenmistry Letters,2007, pp. 1078-1081, vol. 17.
Peifer et al., "Design, Synthesis, and Biological Evaluation of 3,4-Diarylmaleimides as Angiogenesis Inhibitors," J. Med. Chem, 2006, pp. 1271-1281, vol. 49.
Kaffy et al., "Isoxazole-type derivatives related to combretastin A-4, synthesis and biological evaluation," Bioorganic and Medicinal Chemistry, 2006, pp. 4067-4077, vol. 14.
Maya et al., "New naphthylcombretastatins. Modifications on the ethylene bridge," Bioorganic and Medicinal Chemistry, 2005, pp. 2097-2107, vol. 13.
Liou et al., "Concise Synthesis and Structure-Activity Relationships of Combretastatin A-4 Analogues, 1-Aroylindoles and 3-Aroylindoles, as Novel Classes of Potent Antitubulin Agents," J.Med. Chem, 2004, pp. 4247-4257, vol. 47.
Petit et al., "Isolation and structure of combretastatin," Can J. Chem, 1982, pp. 1374-1376, vol. 60. Lin et al., "Interactions of Tubulin with Potent Natural and Synthetic Analogs of the Antimitotic Agent Combretastatin: a Structure-Activity Study," Molecular Pharmacology, 1988, pp. 200-208, vol. 34.
Gurjar et al., "Synthesis and Evaluation of 4/5-Hydroxy-2,3-diaryl(substituted)-cyclopent-2-en-1-ones as cis-Restricted Analogues of Combretastatin A-4 as Novel Anticancer Agents," J. Med. Chem, 2007, pp. 1744-1753, vol. 50.

(Continued)

*Primary Examiner* — Kamal Saeed
*Assistant Examiner* — Kristin Bianchi
(74) *Attorney, Agent, or Firm* — Muncy, Geissler, Olds & Lowe, PLLC

(57) ABSTRACT

An isoxazole derivative is provided. The isoxazole derivative has following formula:

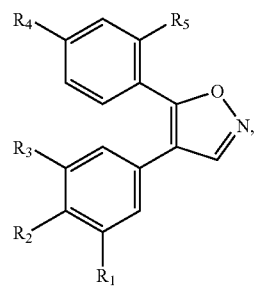

wherein $R_1$, $R_2$, $R_3$, $R_4$ and $R_5$, independently, include hydrogen, hydroxy or $C_1$-$C_{12}$ alkoxy optionally substituted with oxirane, thiirane, aziridine, amino, cycloamino, aminohydroxy or cycloaminohydroxy. The invention also provides a pharmaceutical composition for treatment of osteoporosis and cancer including an isoxazole derivative or a pharmaceutically acceptable salt thereof and a pharmaceutically acceptable carrier.

4 Claims, No Drawings

OTHER PUBLICATIONS

Pirali et al., "Synthesis and Cytotoxic Evaluation of Combretafurans, Potential Scaffolds for Dual-Action Anitumoral Agents," 2006, pp. 5372-5376, vol. 49.

Iron et al., "Medicinal Chemistry of Combretastatin A4: Present and Future Directions," J. Med. Chem, Jun. 1, 2006, pp. 3033-3044, vol. 49—No. 11.

Zhou et al., "Strucutre-Guided Optimization of Estrogen Receptor Binding Affinity and Antagonist Potency of Pyrazolopyrimidines with Basic Side Chains," J. Med Chem, 2007, pp. 399-403, vol. 50.

Compton et al., "Pyrazolo[1,5-α]pyrimidines as estrogen receptor ligands: defining the orientation of a novel heterocyclic core," Bioorganic and Medicinal Chemistry Letters, 2004, pp. 5681-5684, vol. 14.

Compton et al., "Pyrazolo[1,5-α]pyrimidines:Estrogen Receptor Ligands Possessing Estrogen Receptor β Antagonist Activity," 2004, pp. 5872-5893, vol. 47.

Wang et al., "Synthesis, antiproliferative, and antiplatelet activities of oxime- and methyloxime-containing flavone and isoflavone derivatives," Bioorganic and Medicinal Chemistry, 2005, pp. 6045-6053, vol. 13.

Murthy et al., "Synthesis of 4,5-Diarylisoxazole derivatives from Isoflavones," Indian Journal of Chemistry, 1985, pp. 667-669, vol. 24B.

Letourneau et al., "A novel and convenient sythesis of 5-aryl-4-bromo-3-carboxyisoxazoles: useful intermediates for the solid-phase synthesis of 4,5-diarylisoxazoles," Tetrahedron Letters, 2007, pp. 1739-1743, vol. 48.

Denmark et al. "Synthesis of 3,4,5-Trisubstituted Isoxazoles via sequntial [3+2] Cycloaddition/Silicon-Based Cross-Coupling Reactions," J. Org. Chem, 2005, pp. 2839-2842, vol. 70.

Xie et al., "Three-Component, One-Pot Reaction for the Combinatorial Synthesis of 1,3,4-Substituted Pyrazoles," J. Comb. Chem, 2006, pp. 286-288, vol. 8.

Gao et al., "Synthesis of Daidzin Analogues as Potential Agents for Alcohol Abuse," Bioorganic and Medicinal Chemistry, 2003, pp. 4069-4081, vol. 11.

Carmichael et al., "Evaluation of a Tatrazolium-based Semiautomated Colorimetric Assay: Assessment of Chemosensitivity Testing," Cancer Research, Feb. 15, 1987, pp. 936-942, vol. 47.

Crowston et al., "Antimetabolite-Induced Apoptosis in Tenon's Capsule Fibroblasts," IOVS, Feb. 1998, pp. 449- 454, vol. 39-No. 2.

Gregory et al., "An Alizarin red-based assay of mineralization by adherent cells in culture: comparison with cetylpyridinium chloride extraction," Analytical Biochemistry, 2004, pp. 77-84, vol. 329.

* cited by examiner

ISOXAZOLE DERIVATIVES AND PHARMACEUTICAL COMPOSITIONS COMPRISING THE SAME

This application claims priority of Taiwan Patent Application No. 97106587, filed on Feb. 26, 2008, the entirety of which is incorporated by reference herein.

BACKGROUND OF THE INVENTION

1. Field of the Invention

The invention relates to a compound, and in particular, to an isoxazole derivative for treatment of osteoporosis and cancer.

2. Description of the Related Art

The isoxazoles, especially 4,5-diarylisoxazole derivatives (the isoxazole skeleton bearing two neighboring aryl substituents), have been found to possess broad biological effects, including anti-inflammatory (Habeeb, A. G. et. al. *J. Med. Chem.* 2001, 44, 2921; Habeeb, A. G. et. al. *Drug Dev. Res.* 2000, 51, 273; Talley, J. J. Patent No. US 1999/U.S. Pat. No. 5,859,257) and anticancer activities (Zhang, Q. et. al. *J. Med. Chem.* 2007, 50, 749; Sun, C. M. et. al. *Bioorg. Med. Chem. Lett.* 2007, 17, 1078; Peifer, C. et. al. *J. Med. Chem.* 2006, 49, 1271; Kaffy, J. et. al. *Bioorg. Med. Chem.* 2006, 14, 4067; Sanchez Maya, A. B. et. al. *Bioorg. Med. Chem.* 2005, 13, 2097).

Recently, certain structural analogues of 4,5-diarylisoxazole derivatives have been extensively explored as potential anticancer agents. For example, the cytotoxic combretastatin A-4 (Liou, J. P. et. al. *J. Med. Chem.* 2004, 47, 4247; Petit, G. R. et. al. *Can. J. Chem.* 1982, 60, 1374; Lin, C. M. et. al. *Mol. Pharmacol.* 1988, 34, 200) can be considered as an analogue of 4,5-diarylisoxazole in which the isoxazole moiety is replaced with a simple ethylene bridge. Other 4,5-diarylisoxazole analogues, such as the replacement of isoxazole moiety with a cyclopentene ring (Gurjar, M. K. et. al. *J. Med. Chem.* 2007, 50, 1744) or a five membered heterocyclic ring (Pirali, T. et. al. *J. Med. Chem.* 2006, 49, 5372; Tron, G. C. et. al. *J. Med. Chem.* 2006, 49, 3033), have also been synthesized and evaluated for their anticancer activities. Therefore, structural optimization of 4,5-diarylisoxazole has led to the discovery of potential drug candidates. Researchers are interested in the investigation of 4,5-diarylisoxazole derivatives as anti-osteoporotic agents because certain 4,5-diarylisoxazole analogues, in which the isoxazole moiety is replaced with a pyrazolopyrimidine ring (Zhou, H. B. et. al. *J. Med. Chem.* 2007, 50, 399; Compton, D. R. et. al. *Bioorg. Med. Chem.* 2004, 14, 5681; Compton, D. R. et. al. *J. Med. Chem.* 2004, 47, 5872), have been discovered to possess estrogen receptor beta antagonist activity.

Ipriflavone (Kunikata, K. et. al. Patent No. JP 1996/09268187 A; Imamiya, K. et. al. Patent No. JP 1997/11012265 A; Yamazaki, I. et. al. Patent No. EP 1984/136569 A2; Ferrari, M. Patent No. EP 1999/941992 A1; Ferrari, M. Patent No. EP 2002/941992 B1), one of the synthetic isoflavone derivatives, has been approved for the treatment of involutional osteoporosis in some European countries and in Japan.

BRIEF SUMMARY OF THE INVENTION

One embodiment of the invention provides an isoxazole derivative having the following formula:

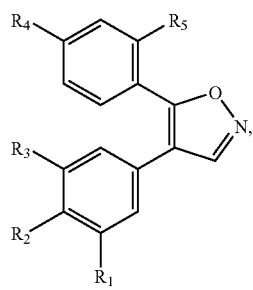

wherein $R_1$, $R_2$, $R_3$, $R_4$ and $R_5$, independently, comprise hydrogen, hydroxy or $C_1$-$C_{12}$ alkoxy optionally substituted with oxirane, thiirane, aziridine, amino, cycloamino, aminohydroxy or cycloaminohydroxy.

One embodiment of the invention provides a pharmaceutical composition comprising a disclosed isoxazole derivative or a pharmaceutically acceptable salt thereof and a pharmaceutically acceptable carrier.

One embodiment of the invention provides a pharmaceutical composition for treatment of osteoporosis comprising a disclosed isoxazole derivative or a pharmaceutically acceptable salt thereof and a pharmaceutically acceptable carrier.

One embodiment of the invention provides a pharmaceutical composition for treatment of cancer comprising a disclosed isoxazole derivative or a pharmaceutically acceptable salt thereof and a pharmaceutically acceptable carrier.

A detailed description of the invention is provided in the following.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

One embodiment of the invention provides an isoxazole derivative having the following formula:

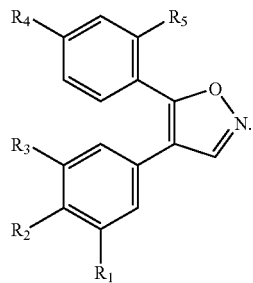

In the formula, $R_1$, $R_2$, $R_3$, $R_4$ and $R_5$ may, independently, comprise hydrogen, hydroxy or $C_1$-$C_{12}$ alkoxy. The $C_1$-$C_{12}$ alkoxy may, optionally, be substituted with oxirane, thiirane, aziridine, amino, cycloamino, aminohydroxy or cycloaminohydroxy.

The isoxazole derivative may be present as a hydrate or as a stereoisomer.

One embodiment of the invention provides a pharmaceutical composition comprising a disclosed isoxazole derivative or a pharmaceutically acceptable salt thereof and a pharmaceutically acceptable carrier.

One embodiment of the invention provides a pharmaceutical composition for treatment of osteoporosis comprising a disclosed isoxazole derivative or a pharmaceutically acceptable salt thereof and a pharmaceutically acceptable carrier.

One embodiment of the invention provides a pharmaceutical composition for treatment of cancer comprising a disclosed isoxazole derivative or a pharmaceutically acceptable salt thereof and a pharmaceutically acceptable carrier.

The pharmaceutically acceptable salts may comprise salts with inorganic acids such as hydrochloride, hydrobromide, sulfate and phosphate, with organic acids such as acetate, maleate, tartrate and methanesulfonate, and with amino acids such as arginine, aspartic acid and glutamic acid.

The pharmaceutically acceptable carrier may comprise any and all solvents, disintegrating agents, binders, excipients, lubricants, absorption delaying agents and the like.

The isoxazole derivative and its pharmaceutical composition effectively inhibit growth of cancer cells and treat osteoporosis. They may be administered parenterally or orally in a suitable pharmaceutical form, for example, sterile aqueous solutions or dispersions, sterile powders, tablets, troches, pills, capsules or the like. They may also be administered along or in conjugation with other anti-osteoporotic and/or anticancer agents, or in combination with any pharmaceutically acceptable carrier. In addition, the pharmaceutical composition may be incorporated into sustained-release preparations and formulations.

The isoxazole derivative is prepared according to the following reaction schemes (Scheme 1 and Scheme 2).

As described in Scheme 1, treatment of 7-hydroxy-3-(4-methoxyphenyl)-4H-chromen-4-one (1) with 2-bromopropane gives 3-(4-methoxyphenyl)-7-isopropoxy-4H-chromen-4-one (2) which is then reacted with NH$_2$OH to give 5-isopropoxy-2-(4-(4-methoxyphenyl)isoxazol-5-yl)phenol (3) in a good overall yield. Reaction of 3 with polyethylenedibromide affords monobromoisoxazoles 4 which are respectively treated with substituted amines to afford the respective aminoalkoxy substituted 4,5-diphenylisokazoles 5.

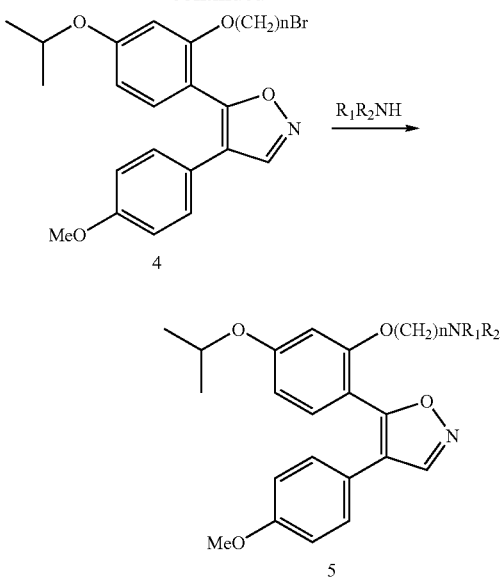

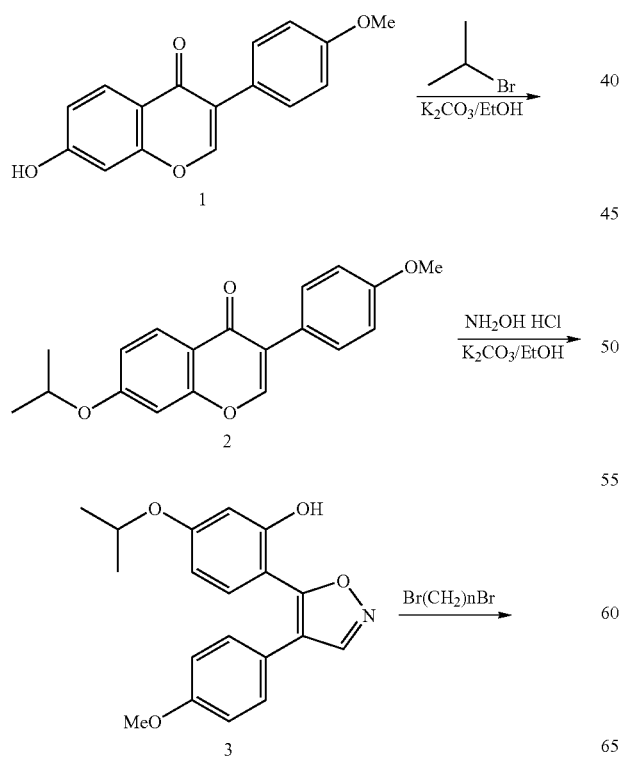

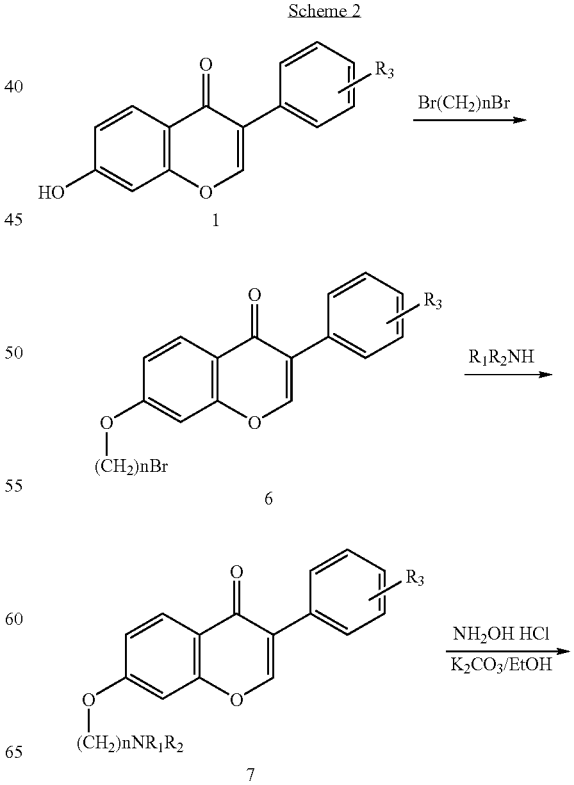

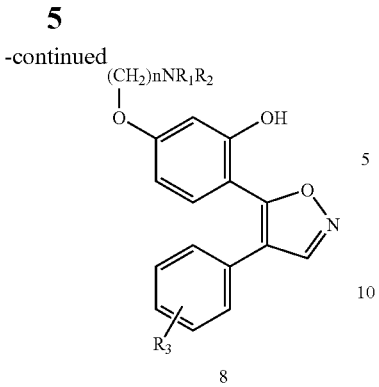

Compound 1 can also be converted into monobromoalkoxy isoflavones 6 which are then aminated to give the respective aminoalkoxy isoflavones 7. Treatment of 7 with $NH_2OH$ respectively affords the respective aminoalkoxy substituted 4,5-diphenylisoxazoles 8 as described in Scheme 2.

The invention report herein acknowledges the conversion of isoflavones into novel 4,5-diphenylisoxazole derivatives by a treatment with $NH_2OH$ (Sree Rama, M. M. et. al. *Indian J. Chem. Section B* 1985, 24B, 667). Other synthetic approaches toward 4,5-diphenylisoxazole derivatives have also been reported recently (Letourneau, J. J. et. al. *Tetrahedron Lett.* 2007, 48, 1739; Denmark, S. E. et. al. *J. Org. Chem.* 2005, 70, 2839; Xie, F. et. al. *J. Comb. Chem.* 2006, 8, 286). Alkylation followed by amination of these 4,5-diphenylisoxazoles gives the desired aminoalkoxy substituted 4,5-diphenylisoxazole derivatives (formula I).

Example 1

Preparation of 7-Isopropoxy-3-(4-methoxyphenyl)-4H-chromen-4-one (2)

A mixture of Formononetin (1, 1.34 g, 5 mmol) (G.Y. Gao, et. al. *Bioorg. Med. Chem.* 2003, 11, 4069), $K_2CO_3$ (0.69 g, 5 mol), 2-bromopropane (1.23 g, 10 mmol) and DMF (10 mL) was refluxed with stirring for 3 hrs (TLC monitoring). The mixture was then cooled and evaporated in vacuo to give a residue which was treated with $H_2O$ (50 mL). The precipitate thus obtained was collected, purified by column chromatography ($MeOH/CH_2Cl_2$=1:100), and crystallization from EtOH to give 2 (1.46 g, 94% yield). M.p.: 245-246° C.
$^1H$-NMR (400 MHz, DMSO-$d_6$): 1.33 (d, 6H), 3.79 (s, 3H, OMe), 4.83 (septet, 1H), 6.98-7.06 (m, 3H), 7.14 (d, 1H), 7.51-7.54 (m, 2H), 8.01 (d, 1H). $^{13}C$-NMR (100 MHz, DMSO-$d_6$): 21.53, 55.13, 70.39, 101.76, 113.59 (2C), 115.56, 117.31, 123.29, 124.09, 127.02, 130.05 (2C), 153.30, 153.46, 157.47, 158.98, 161.95, 174.58.

Example 2

Preparation of 5-Isopropoxy-2-[4-(4-methoxyphenyl)isoxazol-5-yl]phenol (3)

A mixture of 2 (obtained from example 1) (0.31 g, 1 mmol), $NH_2OH$·HCl (0.13 g, 4 mmol), $K_2CO_3$ (0.28 g, 2 mmol) and ethanol (10 mL) was refluxed with stirring for 24 hrs (TLC monitoring). The mixture was then cooled and evaporated in vacuo to give a residue which was treated with $H_2O$ (50 mL). The precipitate thus obtained was collected and crystallized from EtOH to give 3 (0.30 g, 90% yield). M.p.: 148-149° C.
$^1H$-NMR (400 MHz, DMSO-$d_6$): 1.28 (d, 6H), 3.73 (s, 3H, OMe), 4.57 (septet, 1H), 6.47-6.49 (m, 2H), 6.88-6.92 (m, 2H), 7.16 (m, 1H), 6.28-7.37 (m, 2H), 8.92 (s, 1H), 9.95 (br s, 1H, OH). $^{13}C$-NMR (100 MHz, DMSO-$d_6$): 1.80 (2C), 55.7, 69.35, 102.90, 106.59, 107.27, 114.03 (2C), 116.16, 122.37, 127.93 (2C), 131.56, 150.56, 156.93, 158.38, 160.25, 161.93.

Example 3

Preparation of 5-[2-(4-Bromobutoxy)-4-isopropoxyphenyl]-4-(4-methoxyphenyl)isoxazole (4a, n=4)

A mixture of 3 (obtained from example 2) (0.65 g, 2 mmol), $K_2CO_3$ (0.28 g, 2 mmol), 1,4-dibromobutane (0.65 g, 3 mmol) and DMF (5 mL) was heated at 60-70° C. with stirring for 3 hrs (TLC monitoring). The mixture was then cooled and evaporated in vacuo to give a residue which was treated with $H_2O$ (50 mL). The precipitate thus collected was washed with $H_2O$ and then dried to give a crude solid, which was purified by column chromatography ($MeOH/CH_2Cl_2$=1:50) to give 4a as a brown oil (0.69 g, 75% yield).
$^1H$-NMR (400 MHz, DMSO-$d_6$): 1.26 (m, 2H), 1.37 (d, 6H), 1.38 (m, 2H), 2.25 (t, 2H), 3.73 (t, 2H), 3.78 (s, 3H, OMe), 4.60 (septet, 1H), 6.44 (d, 1H), 6.53 (dd, 1H), 6.80-6.84 (m, 2H), 7.18-7.22 (m, 2H), 7.38 (d, 1H), 8.44 (s, 1H). $^{13}C$-NMR (100 MHz, DMSO-$d_6$): 21.95, 22.64, 26.28, 52.28, 55.19, 57.67, 67.69, 69.98, 100.97, 106.29, 109.61, 113.76 (2C), 116.34, 123.34, 128.05 (2C), 131.63, 150.38, 157.54, 158.70, 160.86, 161.92.

Example 4

Preparation of 5-[2-(6-Bromohexyloxy)-4-isopropoxyphenyl]-4-(4-methoxyphenyl)isoxazole (4b, n=6)

A mixture of 3 (obtained from example 2) (0.65 g, 2 mmol), $K_2CO_3$ (0.28 g, 2 mmol), 1,6-dibromohexane (0.73 g, 3 mmol) and DMF (5 mL) was heated at 60-70° C. with stirring for 3 hrs (TLC monitoring). The mixture was then cooled and evaporated in vacuo to give a residue which was treated with $H_2O$ (50 mL). The precipitate thus collected was washed with H₂O and then dried to give a crude solid, which was purified by column chromatography (MeOH/CH₂Cl₂=1:50) to give 4b as a brown oil (0.51 g, 52% yield).

¹H-NMR (400 MHz, CDCl₃): 1.07-1.31 (m, 6H), 1.38 (d, 6H), 1.70-1.77 (m, 2H), 3.34 (t, 2H), 3.69 (t, 2H), 3.80 (s, 3H, OMe), 4.61 (septet, 1H), 6.44 (d, 1H), 6.55 (dd, 1H), 6.83 (m, 2H), 7.21 (m, 2H), 7.42 (d, 1H), 8.45 (s, 1H). ¹³C-NMR (100 MHz, CDCl₃): 22.03, 24.84, 27.68, 28.23, 32.48, 33.84, 55.28, 67.85, 70.04, 101.07, 106.25, 109.81, 113.80, 116.39, 123.60, 128.05, 131.71, 150.48, 157.62, 158.76, 160.91, 161.93.

Example 5

Preparation of 5-[2-(7-Bromoheptyloxy)-4-isopropoxyphenyl]-4-(4-methoxyphenyl)isoxazole (4c, n=7)

A mixture of 3 (obtained from example 2) (0.65 g, 2 mmol), K₂CO₃ (0.28 g, 2 mmol), 1,7-dibromoheptane (0.77 g, 3 mmol) and DMF (5 mL) was heated at 60-70° C. with stirring for 3 hrs (TLC monitoring). The mixture was then cooled and evaporated in vacuo to give a residue which was treated with H₂O (50 mL). The precipitate thus collected was washed with H₂O and then dried to give a crude solid, which was purified by column chromatography (MeOH/CH₂Cl₂=1:50) to give 4c as a pale yellow oil (0.67 g, 67% yield).

¹H-NMR (400 MHz, CDCl₃): 1.05-1.39 (m, 14H), 1.79 (m, 2H), 3.38 (t, 2H), 3.69 (t, 2H), 3.80 (s, 3H, OMe), 4.61 (septet, 1H), 6.45 (d, 1H), 6.55 (dd, 1H), 6.83 (m, 2H), 7.21 (m, 2H), 7.42 (d, 1H), 8.45 (s, 1H). ¹³C-NMR (100 MHz, CDCl₃): 22.04, 25.45, 27.87, 28.28, 32.56, 33.94, 33.99, 52.28, 67.99, 70.03, 101.09, 106.21, 109.81, 113.79, 115.72, 123.62, 128.08, 131.70, 150.50, 157.68, 158.75, 160.91, 161.95.

Example 6

Preparation of 5-{4-Isopropoxy-2-[4-(pyrrolidin-1-yl)butoxy]phenyl}-4-(4-methoxyphenyl)isoxazole (5a, n=4)

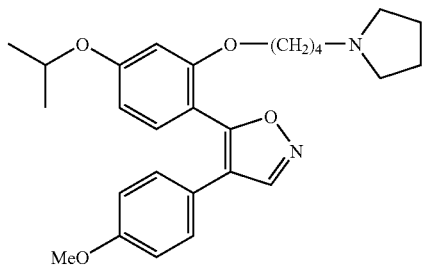

5a

A mixture of 4a (obtained from example 3) (0.46 g, 1 mmol), pyrrolidine (0.11 g, 1.5 mmol) and ethanol (30 mL) was refluxed for 4 h (TLC monitoring). The mixture was then cooled and evaporated in vacuo to give a residue which was treated with H₂O (50 mL). The precipitate thus collected was washed with H₂O and then dried to give a crude solid, which was purified by column chromatography (MeOH/CH₂Cl₂=1:20) and crystallized from EtOH to give 5a (0.32 g, 71% yield). M.p.: 153-154° C.

¹H-NMR (400 MHz, CDCl₃): 1.26 (m, 2H), 1.37 (d, 6H), 1.74-1.81 (m, 4H), 2.34 (m, 3H), 2.48 (m, 5H), 3.73 (m, 2H), 3.80 (s, 3H, OMe), 4.61 (septet, 1H), 6.44 (d, 1H), 6.53 (dd, 1H), 6.81-6.85 (m, 2H), 7.19-7.22 (m, 2H), 7.38 (d, 2H), 8.43 (s, 1H). ¹³C-NMR (100 MHz, CDCl₃): 22.02 (2C), 23.31 (2C), 24.97, 26.46, 53.96 (2C), 55.26, 55.87, 67.90, 70.04, 101.01, 106.27, 109.66, 113.81 (2C), 116.42, 123.47, 128.14 (2C), 131.70, 150.47, 157.65, 158.76, 160.91, 162.05.

Example 7

Preparation of 4-{4-{5-Isopropoxy-2-[4-(4-methoxyphenyl)isoxazol-5-yl]phenoxy}butyl}morpholine (5b, n=4)

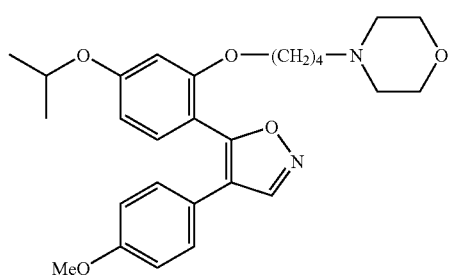

5b

A mixture of 4a (obtained from example 3) (0.46 g, 1 mmol), morpholine (0.13 g, 1.5 mmol) and ethanol (30 mL) was refluxed for 4 h (TLC monitoring). The mixture was then cooled and evaporated in vacuo to give a residue which was treated with H₂O (50 mL). The precipitate thus collected was washed with H₂O and then dried to give a crude solid, which was purified by column chromatography (MeOH/CH₂Cl₂=1:5) and crystallized from EtOH to give 5b as a pale yellow oil (0.34 g, 73% yield).

¹H-NMR (400 MHz, CDCl₃): 1.28 (m, 4H), 1.37 (d, 6H), 2.17-2.23 (m, 2H), 2.37 (m, 4H), 3.69-3.79 (m, 6H), 3.80 (s, 3H, OMe), 4.61 (septet, 1H), 6.45 (d, 1H, J=2.4 Hz), 6.53 (dd, 1H), 6.81-6.85 (m, 2H), 7.19-7.23 (m, 2H), 7.38 (d, 2H), 8.44 (s, 1H). ¹³C-NMR (100 MHz, CDCl₃): 22.03 (2C), 22.57, 26.37, 53.49 (2C), 55.27, 58.39, 66.75, 67.82 (2C), 70.05, 101.11, 106.23, 109.72, 113.82 (2C), 116.41, 123.47, 128.13 (2C), 131.74, 150.44, 157.67, 158.76, 160.92, 162.05.

Example 8

Preparation of 5-{4-Isopropoxy-2-[4-(piperazin-1-yl)butoxy]phenyl}-4-(4-methoxyphenyl)isoxazole (5c, n=4)

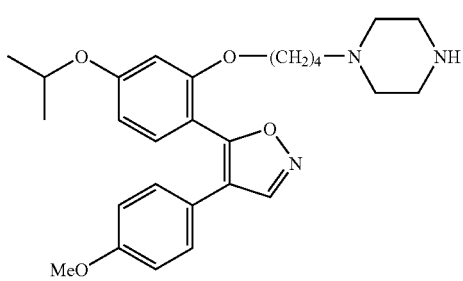

A mixture of 4a (obtained from example 3) (0.46 g, 1 mmol), piperazine (0.13 g, 1.5 mmol) and ethanol (30 mL) was refluxed for 4 h (TLC monitoring). The mixture was then cooled and evaporated in vacuo to give a residue which was treated with H$_2$O (50 mL). The precipitate thus collected was washed with H$_2$O and then dried to give a crude solid, which was purified by column chromatography (MeOH/CH$_2$Cl$_2$=1:5) and crystallized from EtOH to give 5c as a colorless oil (0.21 g, 45% yield).

$^1$H-NMR (400 MHz, DMSO-d$_6$): 1.29 (m, 4H), 1.37 (d, 6H), 2.28 (t, 2H), 2.68 (m, 4H), 3.20 (m, 4H), 3.75 (t, 2H), 3.79 (s, 3H, OMe), 4.61 (septet, 1H), 6.44 (d, 1H), 6.53 (dd, 1H), 6.80-6.84 (m, 2H), 7.19-7.22 (m, 2H), 7.36 (d, 2H), 8.48 (s, 1H). $^{13}$C-NMR (100 MHz, DMSO-d$_6$): 21.96 (2C), 22.55, 26.07, 43.63 (2C), 49.67 (2C), 55.28, 57.29, 67.55, 70.01, 101.02, 106.32, 109.58, 113.81 (2C), 116.37, 123.21, 128.05 (2C), 131.68, 150.39, 157.58, 158.72, 160.89, 161.96. Anal. calcd for C$_{27}$H$_{35}$N$_3$O$_4$.0.9HBr.1.1H$_2$O: C, 57.2; H, 6.79; N, 7.41; found: C, 57.49; H, 6.92; N, 7.04.

Example 9

Preparation of 5-{4-Isopropoxy-2-[4-(piperidin-1-yl)butoxy]phenyl}-4-(4-methoxyphenyl)isoxazole (5d, n=4)

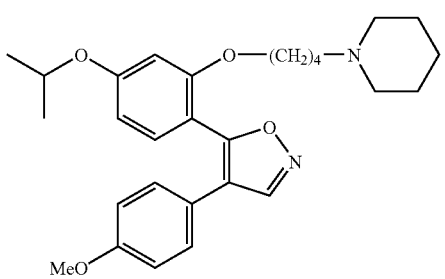

A mixture of 4a (obtained from example 3) (0.46 g, 1 mmol), piperidine (0.13 g, 1.5 mmol) and ethanol (30 mL) was refluxed for 4 h (TLC monitoring). The mixture was then cooled and evaporated in vacuo to give a residue which was treated with H$_2$O (50 mL). The precipitate thus collected was washed with H$_2$O and then dried to give a crude solid, which was purified by column chromatography (MeOH/CH$_2$Cl$_2$=1:5) and crystallized from EtOH to give 5d as a brown oil (0.41 g, 88% yield).

$^1$H-NMR (400 MHz, CDCl$_3$): 1.33 (m, 2H), 1.37 (d, 6H), 1.44-1.46 (m, 2H), 1.54-4.66 (m, 3H), 1.78-1.89 (m, 5H), 2.67 (t, 2H), 3.04 (t, 2H), 3.81 (s, 3H, OMe), 3.84 (t, 2H), 4.61 (septet, 1H), 6.46 (d, 1H), 6.52 (dd, 1H), 6.84-6.85 (m, 2H), 7.21-7.23 (m, 2H), 7.29 (d, 2H), 8.45 (s, 1H). $^{13}$C-NMR (100 MHz, CDCl$_3$): 21.46, 22.00 (2C), 22.57, 23.27, 25.97, 44.52, 47.89, 53.32 (2C), 55.32 (2C), 57.44, 67.63, 70.17, 101.05, 106.74, 109.30, 114.06 (2C), 116.58, 122.83, 128.23 (2C), 131.80, 150.39, 157.58, 158.92, 161.08, 162.26.

Example 10

Preparation of 5-{4-Isopropoxy-2-[6-(pyrrolidin-1-yl)hexyloxy]phenyl}-4-(4-methoxyphenyl)isoxazole (5e, n=6)

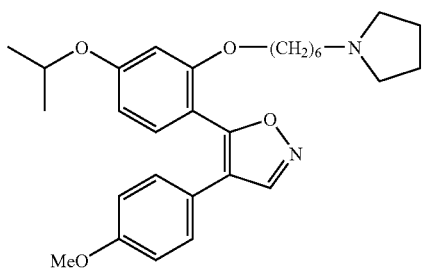

A mixture of 4b (obtained from example 4) (0.48 g, 1 mmol), piperidine (0.11 g, 1.5 mmol) and ethanol (30 mL) was refluxed for 4 h (TLC monitoring). The mixture was then cooled and evaporated in vacuo to give a residue which was treated with H$_2$O (50 mL). The precipitate thus collected was washed with H$_2$O and then dried to give a crude solid, which was purified by column chromatography (MeOH/CH$_2$Cl$_2$=1:5) and crystallized from EtOH to give 5e as a pale yellow oil (0.37 g, 77% yield).

$^1$H-NMR (400 MHz, CDCl$_3$): 1.14 (m, 2H), 1.26 (m, 4H), 1.34 (m, 4H), 1.37 (d, 6H), 2.69 (m, 3H), 2.88 (m, 5H), 3.72 (t, 2H), 3.80 (s, 3H, OMe), 4.62 (septet, 1H), 6.45 (d, 1H), 6.52 (dd, 1H), 6.82-6.84 (m, 2H), 7.20-7.22 (m, 2H), 7.35 (d, 2H), 8.44 (s, 1H). $^{13}$C-NMR (100 MHz, CDCl$_3$): 22.04 (2C), 23.36 (2C), 25.26, 26.51, 28.15, 29.68, 53.72, 55.31, 55.34, 55.74, 67.80, 70.09, 101.11, 106.40, 109.65, 113.91, 114.47, 116.53, 123.35, 128.17, 129.61, 131.70, 150.48, 157.78, 158.81, 160.98, 162.18.

Example 11

Preparation of 4-{6-{5-Isopropoxy-2-[4-(4-methoxyphenyl)isoxazol-5-yl]phenoxy}hexyl}morpholine (5f, n=6)

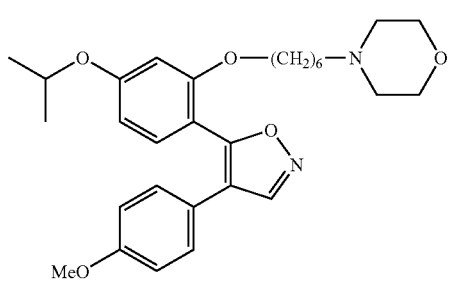

A mixture of 4b (obtained from example 4) (0.48 g, 1 mmol), morpholine (0.13 g, 1.5 mmol) and ethanol (30 mL) was refluxed for 4 h (TLC monitoring). The mixture was then cooled and evaporated in vacuo to give a residue which was treated with $H_2O$ (50 mL). The precipitate thus collected was washed with $H_2O$ and then dried to give a crude solid, which was purified by column chromatography (MeOH/$CH_2Cl_2$=1:5) and crystallized from EtOH to give 5f as a pale yellow oil (0.34 g, 68% yield).

$^1$H-NMR (400 MHz, $CDCl_3$): 1.08-1.24 (m, 6H), 1.38 (d, 6H), 2.25-2.29 (m, 2H), 2.43 (m, 4H), 3.68-3.74 (m, 6H), 3.80 (s, 3H, OMe), 4.60 (septet, 1H), 6.44 (d, 1H), 6.53 (dd, 1H), 6.80-6.84 (m, 2H), 7.18-7.22 (m, 2H), 7.39 (d, 2H), 8.43 (s, 1H), $^{13}$C-NMR (100 MHz, $CDCl_3$): 22.04 (2C), 25.59, 26.24, 27.04, 28.36, 53.67 (2C), 55.27, 58.97, 66.87, 67.96 (2C), 70.03, 101.11, 106.17, 109.79, 113.78 (2C), 116.41, 123.62, 128.11 (2C), 131.70, 150.50, 157.72, 158.73, 160.89, 162.03.

Example 12

Preparation of 5-{4-Isopropoxy-2-[6-(piperazin-1-yl)hexyloxy]phenyl}-4-(4-methoxyphenyl)isoxazole (5 g, n=6)

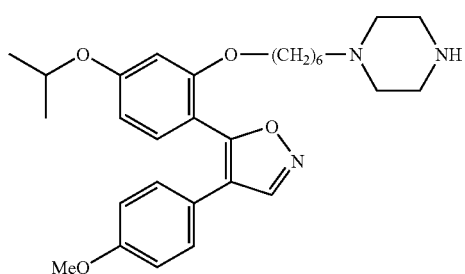

A mixture of 4b (obtained from example 4) (0.48 g, 1 mmol), piperazine (0.13 g, 1.5 mmol) and ethanol (30 mL) was refluxed for 4 hrs (TLC monitoring). The mixture was then cooled and evaporated in vacuo to give a residue which was treated with $H_2O$ (50 mL). The precipitate thus collected was washed with $H_2O$ and then dried to give a crude solid, which was purified by column chromatography (MeOH/$CH_2Cl_2$=1:5) and crystallized from EtOH to give 5 g as a pale yellow oil (0.34 g, 68% yield).

$^1$H-NMR (400 MHz, $CDCl_3$): 1.09-1.26 (m, 6H), 1.38 (d, 6H), 2.10 (m, 4H), 2.23 (m, 2H), 2.40 (m, 4H), 2.89 (t, 2H), 3.75 (t, 2H), 3.80 (s, 3H, OMe), 4.60 (septet, 1H), 6.44 (d, 1H), 6.53 (dd, 1H), 6.80-6.84 (m, 2H), 7.18-7.22 (m, 2H), 7.40 (d, 2H), 8.44 (s, 1H). $^{13}$C-NMR (100 MHz, $CDCl_3$): 22.04 (2C), 25.61, 26.41, 27.16, 28.38, 45.91 (2C), 46.88, 54.36, 55.27, 59.19, 68.03, 70.04, 101.12, 106.22, 109.82, 113.80 (2C), 116.42, 123.63, 128.11 (2C), 131.69, 150.49, 157.73, 158.75, 160.91, 162.03.

Example 13

Preparation of 5-{4-isopropoxy-2-[6-(piperidin-1-yl)hexyloxy]phenyl}-4-(4-methoxyphenyl)isoxazole (5h, n=6)

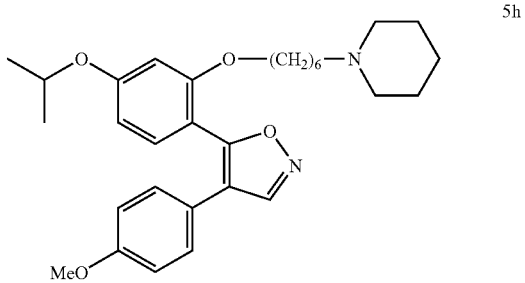

A mixture of 4b (obtained from example 4) (0.48 g, 1 mmol), piperidine (0.13 g, 1.5 mmol) and ethanol (30 mL) was refluxed for 4 hrs (TLC monitoring). The mixture was then cooled and evaporated in vacuo to give a residue which was treated with $H_2O$ (50 mL). The precipitate thus collected was washed with $H_2O$ and then dried to give a crude solid, which was purified by column chromatography (MeOH/$CH_2Cl_2$=1:5) and crystallized from EtOH to give 5h as a brown oil (0.35 g, 71% yield).

$^1$H-NMR (400 MHz, $CDCl_3$): 1.10-1.24 (m, 5H), 1.37 (d, 6H), 1.42-1.54 (m, 4H), 1.64-1.70 (m, 4H), 2.30-2.34 (m, 3H), 2.48 (m, 4H), 3.68 (t, 2H), 3.80 (s, 3H, OMe), 4.61 (septet, 1H), 6.44 (d, 1H), 6.53 (dd, 1H), 6.81-6.84 (m, 2H), 7.18-7.22 (m, 2H), 7.39 (d, 2H), 8.44 (s, 1H). $^{13}$C-NMR (100 MHz, $CDCl_3$): 22.04 (2C), 24.03, 25.29, 25.55 (2C), 26.06, 27.14, 28.33, 54.30 (2C), 55.29, 59.05, 68.00, 70.06, 101.11, 106.30, 109.80, 113.83 (2C), 116.46, 123.60, 128.14 (2C), 131.69, 150.51, 157.75, 158.78, 160.94, 162.07.

Example 14

Preparation of 5-{4-Isopropoxy-2-[7-(pyrrolidin-1-yl)heptyloxy]phenyl}-4-(4-methoxyphenyl)isoxazole (5i, n=7)

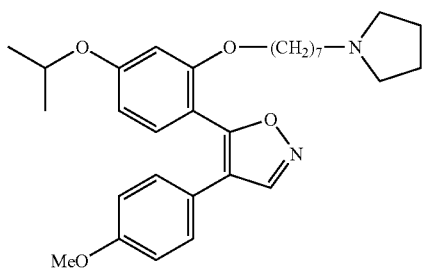

A mixture of 4c (obtained from example 5) (0.50 g, 1 mmol), piperidine (0.11 g, 1.5 mmol) and ethanol (30 mL) was refluxed for 4 hrs (TLC monitoring). The mixture was then cooled and evaporated in vacuo to give a residue which was treated with $H_2O$ (50 mL). The precipitate thus collected was washed with $H_2O$ and then dried to give a crude solid, which was purified by column chromatography (MeOH/$CH_2Cl_2$=1:5) and crystallized from EtOH to give 5i as a pale yellow oil (0.34 g, 69% yield).

$^1$H-NMR (400 MHz, CDCl$_3$): 1.07-1.39 (m, 14), 1.71 (m, 2H), 1.03 (m, 4H), 2.78 (m, 2H), 3.03 (m, 4H), 3.71 (t, 2H), 3.80 (s, 3H, OMe), 4.61 (septet, 1H), 6.44 (d, 1H), 6.53 (dd, 1H), 6.81-6.89 (m, 3H), 7.21 (m, 2H), 7.38 (d, 1H), 8.47 (s, 1H). $^{13}$C-NMR (100 MHz, CDCl$_3$): 21.94, 22.04, 23.35 (2C), 25.59, 26.40, 26.86, 28.21, 28.55, 53.71, 55.32, 55.34, 55.79, 67.98, 70.08, 101.05, 106.34, 109.69, 113.86, 114.52, 116.50, 123.47, 128.14, 129.62, 131.68, 150.54, 157.76, 158.79, 160.98, 162.12.

Example 15

Preparation of 4-{7-{5-isopropoxy-2-[4-(4-methoxyphenyl)isoxazol-5-yl]phenoxy}heptyl}morpholine (5j, n=7)

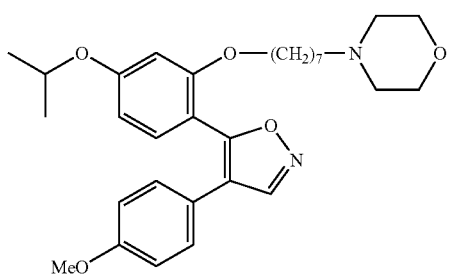

A mixture of 4c (obtained from example 5) (0.50 g, 1 mmol), morpholine (0.13 g, 1.5 mmol) and ethanol (30 mL) was refluxed for 4 hrs (TLC monitoring). The mixture was then cooled and evaporated in vacuo to give a residue which was treated with $H_2O$ (50 mL). The precipitate thus collected was washed with $H_2O$ and then dried to give a crude solid, which was purified by column chromatography (MeOH/$CH_2Cl_2$=1:5) and crystallized from EtOH to give 5j as a brown oil (0.44 g, 86% yield).

$^1$H-NMR (400 MHz, CDCl$_3$): 1.06-1.23 (m, 8H), 1.32-1.46 (m, 8H), 2.27 (m, 2H), 2.43 (m, 4H), 3.66 (t, 2H), 3.71 (m, 4H), 3.80 (s, 3H, OMe), 4.61 (septet, 1H), 6.44 (d, 1H), 6.53 (dd, 1H), 6.80-6.84 (m, 2H), 7.19-7.22 (m, 2H), 7.40 (d, 2H), 8.44 (s, 1H). $^{13}$C-NMR (100 MHz, CDCl$_3$): 22.03 (2C), 25.58, 26.40, 27.28, 28.32, 29.11, 53.73 (2C), 55.25, 59.11, 66.93 (2C), 68.04, 70.01, 101.07, 106.11, 109.77, 113.76 (2C), 116.40, 123.63, 128.10 (2C), 131.68, 150.52, 157.71, 158.72, 160.87, 162.01.

Example 16

Preparation of 5-{4-Isopropoxy-2-[7-(piperazin-1-yl)heptyloxy]phenyl}-(4-methoxyphenyl)isoxazole (5k, n=7)

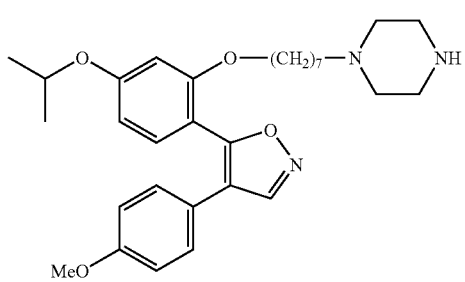

A mixture of 4c (obtained from example 5) (0.50 g, 1 mmol), piperazine (0.13 g, 1.5 mmol) and ethanol (30 mL) was refluxed for 4 hrs (TLC monitoring). The mixture was then cooled and evaporated in vacuo to give a residue which was treated with $H_2O$ (50 mL). The precipitate thus collected was washed with $H_2O$ and then dried to give a crude solid, which was purified by column chromatography (MeOH/$CH_2Cl_2$=1:5) and crystallized from EtOH to give 5k as a pale yellow oil (0.39 g, 77% yield).

$^1$H-NMR (400 MHz, CDCl$_3$): 1.07-1.18 (m, 8H), 1.31-1.53 (m, 8H), 2.34 (m, 2H), 2.54 (m, 4H), 3.01 (m, 4H), 3.68 (t, 2H), 3.79 (s, 3H, OMe), 4.61 (septet, 1H), 6.44 (d, 1H), 6.53 (dd, 1H), 6.80-6.84 (m, 2H), 7.18-7.22 (m, 2H), 7.40 (d, 2H), 8.44 (s, 1H). $^{13}$C-NMR (100 MHz, CDCl$_3$): 22.04 (2C), 25.57, 26.22, 27.21, 28.32, 29.01, 29.68, 45.16 (2C), 53.09, 55.28, 58.86, 68.06, 70.04, 101.11, 106.20, 109.79, 113.80, 114.46, 116.43, 123.62, 128.12, 129.65, 131.69, 150.52, 157.75, 158.75, 160.91, 162.05.

Example 17

Preparation of 5-{4-Isopropoxy-2-[7-(piperidin-1-yl)heptyloxy]phenyl}-4-(4-methoxyphenyl)isoxazole (5l, n=7)

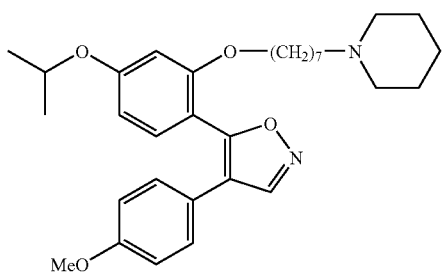

A mixture of 4c (obtained from example 5) (0.50 g, 1 mmol), piperidine (0.13 g, 1.5 mmol) and ethanol (30 mL) was refluxed for 4 hrs (TLC monitoring). The mixture was then cooled and evaporated in vacuo to give a residue which was treated with $H_2O$ (50 mL). The precipitate thus collected was washed with $H_2O$ and then dried to give a crude solid, which was purified by column chromatography (MeOH/$CH_2Cl_2$=1:5) and crystallized from EtOH to give 5l as a brown oil (0.40 g, 78% yield).

$^1$H-NMR (400 MHz, CDCl$_3$): 1.07-1.21 (m, 8H), 1.30-1.39 (m, 8H), 1.60 (m, 2H), 1.81 (m, 4H), 2.52 (m, 2H), 2.68 (m, 4H), 3.69 (t, 2H), 3.80 (s, 3H, OMe), 4.61 (septet, 1H), 6.44 (d, 1H), 6.53 (dd, 1H), 6.81-6.84 (m, 2H), 7.19-7.22 (m, 2H), 7.39 (d, 2H), 8.46 (s, 1H). $^{13}$C-NMR (100 MHz, CDCl$_3$): 22.03 (2C), 23.35, 24.32, 25.08, 25.55, 27.09, 28.24, 28.75, 28.90, 53.86 (2C), 55.30, 58.53, 68.00, 70.06, 101.06, 106.30, 109.73, 113.83, 114.49, 123.52, 128.12 (2C), 129.62, 131.66, 150.51, 157.74, 158.77, 160.94, 162.07.

Example 18

Preparation of 7-(6-Bromohexyloxy)-3-(4-methoxyphenyl)-4H-chromen-4-one (6a, R$_3$=4-OMe, n=6)

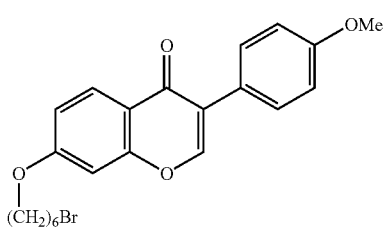

A mixture of Formononetin (1; R$_3$=4-OMe, 0.54 g, 2.0 mmol), K$_2$CO$_3$ (0.28 g, 2.0 mmol) and 1,6-dibromobutane (0.73 g, 3.0 mmol) in DMF (5 mL) was heated at 65-70° C. with stirring for 3 hrs (TLC monitoring). The mixture was then cooled and evaporated in vacuo to give a residue which was treated with $H_2O$ (50 mL). The precipitate thus obtained was collected, purified by column chromatography (MeOH/$CH_2Cl_2$=1:50), and crystallized from EtOH to give 6a (0.69 g, 80% yield). M.p.: 135-136° C.

$^1$H-NMR (400 MHz, DMSO-d$_6$): 1.44-1.48 (m, 4H), 1.76-1.85 (m, 4H), 3.55 (t, 2H), 3.79 (s, 3H, OMe), 4.13 (t, 2H), 7.00 (m, 2H), 7.08 (dd, 1H), 7.15 (d, 1H), 7.53 (m, 2H), 8.02 (d, 1H), 8.42 (s, 1H). $^{13}$C-NMR (100 MHz, DMSO-d$_6$): 24.59, 27.25, 28.23, 32.14, 35.13, 55.14, 68.37, 100.99, 113.61 (2C), 115.03, 117.48, 123.34, 124.07, 126.93, 130.7 (2C), 153.47, 157.44, 158.99, 163.09, 174.63. Anal. calcd for C$_{22}$H$_{23}$BrO$_4$: C, 61.26; H, 5.37; found: C, 61.16; H, 5.38.

Example 19

Preparation of 7-(6-Bromohexyloxy)-3-(3,4-dimethoxyphenyl)-4H-chromen-4-one (6b, R$_3$=3-OMe, 4-OMe, n=6)

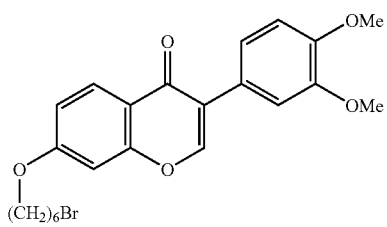

A mixture of 7-hydroxy-3',4'-dimethoxyisoflavone (1; R$_3$=3-OMe, 4-OMe, 0.54 g, 2.0 mmol), K$_2$CO$_3$ (0.28 g, 2.0 mmol) and 1,6-dibromobutane (0.73 g, 3.0 mmol) in DMF (5 mL) was heated at 65-70° C. with stirring for 3 hrs (TLC monitoring). The mixture was then cooled and evaporated in vacuo to give a residue which was treated with $H_2O$ (50 mL). The precipitate thus obtained was collected, purified by column chromatography (MeOH/$CH_2Cl_2$=1:50), and crystallized from EtOH to give 6b (0.73 g, 79% yield). M.p.: 135-136° C.

$^1$H-NMR (400 MHz, DMSO-d$_6$): 1.44-1.48 (m, 4H), 1.75-1.85 (m, 4H), 3.43 (t, 2H), 3.92 (s, 3H, OMe), 3.93 (s, 3H, OMe), 4.05 (t, 2H), 6.84 (d, 1H), 6.92 (d, 1H), 6.97 (dd, 1H), 7.06 (dd, 1H), 7.21 (d, 1H), 7.95 (s, 1H), 8.19 (d, 1H). $^{13}$C-NMR (100 MHz, DMSO-d$_6$): 25.20, 27.82, 28.78, 32.56, 33.72, 55.91, 55.93, 68.39, 100.54, 111.09, 112.44, 114.87, 118.23, 120.98, 124.63, 124.85, 127.67, 148.70, 149.02, 152.20, 157.88, 163.43, 175.89. Anal. calcd for C$_{23}$H$_{25}$BrO$_5$: C, 59.88; H, 5.46; found: C, 59.90; H, 5.41.

Example 20

Preparation of 3-(4-methoxyphenyl)-7-[6-(piperazin-1-yl)hexyloxy]-4H-chromen-4-one (7a, R₃=4-OMe, n=6)

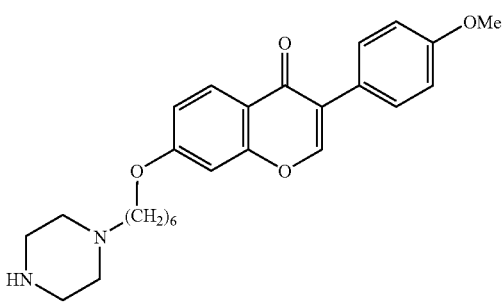

A mixture of 6a (obtained from example 18) (0.43 g, 1.0 mmol), piperazine (0.13 g, 1.5 mmol) in 1,4-dioxane (5 mL) was heated at 65-70° C. with stirring for 14 hrs (TLC monitoring). The mixture was then cooled and evaporated in vacuo to give a residue which was treated with H₂O (50 mL). The resulting precipitate was collected and purified by column chromatography (MeOH/CH₂Cl₂=1:10) to give 7a (0.21 g, 48% yield). M.p.: 198-199° C.

¹H NMR (400 MHz, DMSO-d₆): 1.35 (m, 2H), 1.44 (m, 4H), 1.76 (m, 2H), 2.33 (t, 2H), 2.54 (m, 4H), 3.05 (m, 4H), 3.79 (s, 3H, OMe), 4.12 (t, 2H), 7.00 (m, 2H), 7.07 (dd, 1H), 7.14 (d, 1H), 7.53 (m, 2H), 8.02 (d, 2H), 8.42 (s, 1H). ¹³C-NMR (100 MHz, DMSO-d₆): 25.33, 25.88, 26.47, 28.37, 43.10 (2C), 49.52 (2C), 55.16, 57.37, 68.46, 100.97, 133.61 (2C), 115.04, 117.47, 123.34, 124.05, 126.94, 130.7 (2C), 153.47, 157.44, 159.00, 163.10, 174.63. Anal. calcd for C₂₆H₃₂N₂O₄·0.8HBr·0.4H₂O: C, 60.53; H, 6.57; N, 5.43; found: C, 60.45; H, 5.38.

Example 21

Preparation of 3-(3,4-Dimethoxyphenyl)-7-[6-(piperidin-1-yl)hexyloxy]-4H-chromen-4-one (7b, R₃=3-OMe, 4-OMe, n=6)

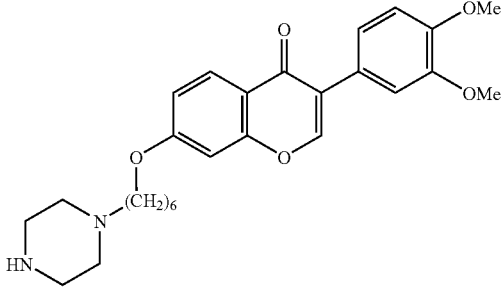

A mixture of 6b (obtained from example 19) (0.46 g, 1.0 mmol), piperidine (0.13 g, 1.5 mmol) in 1,4-dioxane (5 mL) was heated at 65-70° C. with stirring for 14 hrs (TLC monitoring). The mixture was then cooled and evaporated in vacuo to give a residue which was treated with H₂O (50 mL). The resulting precipitate was collected and purified by column chromatography (MeOH/CH₂Cl₂=1:10) to give 7b (0.21 g, 45% yield). M.p.: 181-182° C.

¹H-NMR (400 MHz, CDCl₃): 1.42-1.50 (m, 3H), 1.54-1.61 (m, 2H), 1.83-1.92 (m, 4H), 1.95-2.03 (m, 3H), 2.30-2.40 (m, 2H), 2.61-2.70 (m, 2H), 2.93-2.99 (m, 2H), 3.56-3.59 (m, 2H), 3.92 (s, 3H, OMe), 3.93 (s, 3H, OMe), 4.04 (t, 2H), 6.84 (d, 1H), 6.92 (d, 1H), 6.97 (dd, 1H), 7.05 (dd, 1H), 7.21 (d, 1H), 7.95 (s, 1H), 8.19 (d, 1H). ¹³C-NMR (100 MHz, DMSO-d₆): 22.03, 22.40, 23.42, 25.42, 26.49, 28.62, 53.18, 55.91, 55.93, 57.34, 68.19, 100.57, 111.12, 112.48, 114.86, 118.25, 121.00, 124.63, 124.83, 127.64, 148.71, 149.04, 152.24, 157.88, 163.33, 175.87. Anal. calcd for C₂₈H₃₅NO₅·0.6H₂O·0.8HBr: C, 61.31; H, 6.81; N, 2.55; found: C, 61.52; H, 6.66; N, 2.58.

Example 22

Preparation of 2-(4-(4-Methoxyphenyl)isoxazol-5-yl)-5-(4-(piperazin-1-yl)butoxy)phenol (8a, R₃=4-OMe, n=6)

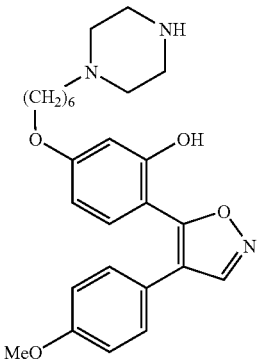

A mixture of 7a (obtained from example 20) (0.44 g, 1.0 mmol), K₂CO₃ (0.28 g, 2.0 mmol) and hydroxylamine hydrochloride (0.13 g, 4.0 mmol) in EtOH (10 mL) was refluxed with stirring for 24 hrs (by TLC monitoring). The mixture was then cooled and evaporated in vacuo to give a residue which was treated with H₂O (50 mL). The resulting precipitate was collected and crystallized from EtOH to give 8a (0.39 g, 87% yield). M.p.: 192-193° C.

¹H NMR (400 MHz, DMSO-d₆): 1.37-1.48 (m, 4H), 1.72-1.76 (m, 4H), 3.09 (m, 2H), 3.30 (m, 4H), 3.45 (m, 4H), 3.74 (s, 3H, OMe), 3.97 (t, 2H), 6.50 (dd, 1H), 6.55 (d, 1H), 6.90 (m, 2H), 7.17 (d, 2H), 7.29 (m, 2H), 8.93 (s, 1H), 10.09 (br s, 1H, OH). ¹³C-NMR (100 MHz, DMSO-d₆): 22.95, 25.02, 25.70, 28.35, 47.66 (2C), 55.10 (2C), 55.47, 67.33, 102.04, 105.77, 107.52, 114.04 (2C), 116.20, 122.35, 127.93 (2C), 131.54, 150.57, 156.99, 158.39, 161.37, 161.94. Anal. calcd for C₂₈H₃₅NO₄·0.9H₂O·0.5HBr: C, 65.83; H, 7.37; N, 2.74; found: C, 65.76; H, 7.27; N, 2.75.

Example 23

Preparation of 2-[4-(3,4-Dimethoxyphenyl)isoxazol-5-yl]-5-([6-(piperidin-1-yl)hexyloxy]phenol (8b, $R_3$=3-OMe, 4-OMe, n=6)

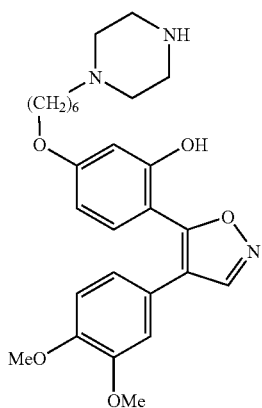

A mixture of 7b (obtained from example 21) (0.47 g, 1.0 mmol), $K_2CO_3$ (0.28 g, 2.0 mmol) and hydroxylamine hydrochloride (0.13 g, 4.0 mmol) in EtOH (10 mL) was refluxed with stirring for 24 rs h (by TLC monitoring). The mixture was then cooled and evaporated in vacuo to give a residue which was treated with $H_2O$ (50 mL). The resulting precipitate was collected and crystallized from EtOH to give 8b (0.23 g, 47% yield). M.p.: 86-87° C.

$^1$H-NMR (400 MHz, $CDCl_3$): 1.32-1.51 (m, 8H), 1.1.63-1.72 (m, 10H), 2.89 (m, 2H), 3.61 (s, 3H, OMe), 3.73 (s, 3H, OMe), 3.97 (t, 2H), 6.51 (dd, 1H), 6.55 (d, 1H), 6.89-6.99 (m, 3H), 7.18 (d, 1H), 8.99 (s, 1H), 10.09 (br s, 1H, OH). $^{13}$C-NMR (100 MHz, DMSO-$d_6$): 21.73, 22.78, 23.39, 25.10 (2C), 25.96, 28.35, 52.16 (2C), 55.22, 55.48, 56.07, 67.39, 102.02, 105.80, 107.60, 110.57, 111.87, 116.47, 119.10, 122.51, 131.71, 148.01, 148.57, 150.57, 157.05, 161.40, 162.04.

Example 24

Cytotoxicity Assay

MCF-7 cells (human breast adenocarcinoma), NCI-H460 cells (non-small-cell lung cancer) and SF-268cells (glioblastoma cells) were cultured in a Dulbecco's modified Eagle's medium supplemented with a 10% fetal calf serum and a nonessential amino acid (Life Technologies, Inc.) and maintained at 37° C. in a humidified incubator with 5% $CO_2$.

Human cancer cells were seeded in 96-well microtiter plates at a density of 6500, 2500 and 7500 cells/well in 100 μl of culture medium for MCF-7, NCI-H460, and SF-268, respectively. After an overnight adaptation period, 20 μg/ml (final concentration) of test compounds in serum-free medium were added to individual wells. Cells were treated with test compounds for 3 days. Cell viability was determined by the 5-[3-(carboxymethoxy)-phenyl]-2-(4,5-dimethylthiazolyl)-3-(4-sulfophenyl)tetrazolium salt (MTS) reduction assay. Actinomycin D (10 μM, final concentration) and DMSO (0.1%, final concentration) were used as positive and vehicle controls, respectively. Results were expressed as a % of the DMSO control.

Example 25

Cell Culture and Drug Treatment

Human adipose tissue derived stem cells (hADSCs), which is derived from adipose tissue, were selected an maintained in a keratinocyte SFM medium (Gibco BRL, Gaithersburg, Md.) supplemented with 5% FBS, 100 U/ml of penicillin and streptomycin. They exhibited osteogenic properties in the Dulbecco modified Eagle medium (Gibco BRL, Gaithersburg, Md.) containing 10% fetal bovine serum and 50 μg/mL sodium ascorbate in a humidified atmosphere of 5% $CO_2$ at 37° C., and the medium was changed every 2 days.

New synthetic compounds were dissolved in DMSO to a final concentration of 10 mM and stored at −20° C. The concentration used was 10 μM and freshly diluted to the medium with a final concentration of DMSO at 0.1%. Control cultures were treated with the same amount of DMSO as used in the corresponding experiments.

Example 26

Cell Viability by MTT [3-(4,5-dimethylthiazol-2-yl)-2,5-diphenyltetrazolium bromide] Assay The MTT assay is a calorimetric assay based on the ability of the viable cells to reduce a soluble yellow tetrazolium salt to blue formazan crystals (Carmichael, J. et. el. *Cancer Research* 1987, 47, 936). After compound treatments, 350 μL of MTT solution (0.5 μg/mL in PBS) were added to each well and incubated for 4 hrs. DMSO was then added for another 0.5 hrs to thoroughly dissolve the dark blue crystals. The absorbance at 570 nm was measured with an ELISA reader. Inhibition of mitochondrial metabolism was shown as relative activity (% of control).

Example 27

Cytotoxicity Assay by Lactate Dehydrogenase (LDH) Leakage

Lactate dehydrogenase (LDH) leakage from cells was measured to quantify the cytotoxicity by using a cytotoxicity detection kit (Roche, Germany) (Crowston, J. G. et al *Invest. Ophthalmol. Vis. Sci.* 1998, 39, 449). Cells were previously seeded into 48-well plates ($4 \times 10^4$ cells/well). After a drug treatment, the supernatants and cell layers of the cultures were collected for assay. According to the manufacturer's guidelines for the detection kit, cell layers were lysed with 1% TritonX-100, and cell lysates and supernatants were assayed in a 96-well plate, respectively. Briefly, 100 μL of catalyst solution was added in each assay well for 20 min. Absorbance was measured with an ELISA reader with a 490 nm filter. LDH leakage was shown as relative activity (% of total cell toxicity).

Example 28

Osteogenic Differentiation and Quantification of Minteralization

Osteogenic differentiation was induced by culturing cells in an osteo-induction medium (OIM, 10% FBS, 0.1 μM dexamethasone, 10 mM β-glycerophosphate, and L-Ascorbic 2 phosphate 100 μM in low glucose DMEM) for 7-14 days. The extracellular matrix calcification was estimated by using an Alizarin red S stain (Carl, A. et al *Anal. Biochem.* 2004, 329, 77). The Alizarin red S-stained mineral was quantified by the osteogenesis quantification kit (CHEMICON®).

It was demonstrated that the aminoalkoxy substituted 4,5-diphenylisoxazole derivatives (formula I) exhibited 100% inhibition on the growth of breast cancer (MCF7), non-small cell lung cancer (NCI-H460), and CNS cancer (SF-268) at a concentration of 20 μg/mL. Among them, 5-{4-isopropoxy-2-[6-(piperazin-1-yl)hexyloxy]phenyl}-4-(4-methoxyphenyl)isoxazole (5 g, n=6), 5-{4-isopropoxy-2-[6-(piperidin-1-yl)hexyloxy]phenyl}-4-(4-methoxyphenyl)isoxazole (5h, n=6), and 5-{4-Isopropoxy-2-[7-(piperazin-1-yl)heptyloxy]phenyl}-4-(4-methoxyphenyl)isoxazole (5k, n=7) were able to significantly inhibit the growth of the above three cancer cells (MCF7, NCI-H460, and SF-268) at a concentration of 4 μg/mL respectively, as shown in Table 2.

It was also demonstrated that the aminoalkoxy substituted 4,5-diphenylisoxazole derivatives (formula I) are able to induce osteoblast activity (mineralization in hADSCs; Table 1). Among them, 5-{4-isopropoxy-2-[4-(pyrrolidin-1-yl)butoxy]phenyl}-4-(4-methoxyphenyl)isoxazole (5a, n=4) and 5-{4-isopropoxy-2-[6-(pyrrolidin-1-yl)hexyloxy]phenyl}-4-(4-methoxyphenyl)isoxazole (5e, n=6) for example, were more active than ipriflavone in the promotion of osteoblast activity. Both compounds 5a and 5e are non-cytotoxic (0% of cell cytotoxicity; Table 1) and therefore, are potential anti-osteoporotic drug candidates for further development.

TABLE 1

Cell viability, cell cytotoxicity, and osteogenic mineralization in hADSCs of isoxazole derivatives at a concentration of 10 μM.

| Compd. | n | $NR_1R_2$ | Cell viability (3 days, MTT) | Cell cytotoxicity (3 days, LDH) | Mineralization (10 days) |
|---|---|---|---|---|---|
| 3 | — | — | 6 | 68 | 277 |
| 5a | 4 | 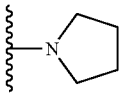 | 71 | 0 | 194 |
| 5b | 4 | 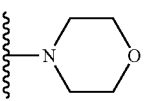 | 58 | 13 | 130 |
| 5c | 4 | 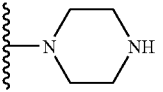 | 86 | 33 | 108 |
| 5d | 4 | 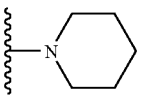 | 78 | 0 | 114 |
| 5e | 6 | 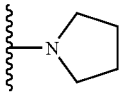 | 64 | 0 | 158 |
| 5f | 6 | 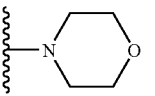 | 53 | 17 | 0 |
| 5g | 6 | 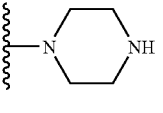 | 60 | 0 | 137 |
| 5h | 6 | 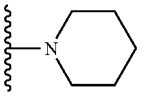 | 57 | 0 | 0 |
| 5i | 7 | 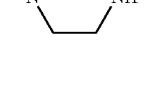 | 63 | 0 | 0 |
| 5j | 7 | 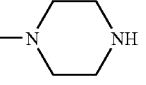 | 54 | 12 | 158 |
| 5k | 7 | 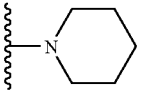 | 68 | 0 | 53 |
| 5l | 7 |  | 58 | 0 | 124 |
| 8a | 6 |  | 64 | 0 | 36 |
| 8b | 6 |  | 11 | 41 | 285 |
| Ipriflavone | | | 77% | 0% | 100% |

TABLE 2

Antiproliferative of isoxazole derivatives.

| Compd. | n | NR₁R₂ | MCF7 (Breast) 20 μg/mL | MCF7 (Breast) 4 μg/mL | NCI-H460 (Lung) 20 μg/mL | NCI-H460 (Lung) 4 μg/mL | SF-268 (CNS) 20 μg/mL | SF-268 (CNS) 4 μg/mL |
|---|---|---|---|---|---|---|---|---|
| 5a | 4 | pyrrolidine | 1 | 83 | 1 | 81 | 2 | 121 |
| 5b | 4 | morpholine | 4 | 63 | 1 | 52 | 3 | 58 |
| 5c | 4 | piperazine | −1 | 7 | 0 | 29 | −2 | 68 |
| 5d | 4 | piperidine | 1 | 90 | 1 | 68 | 2 | 119 |
| 5e | 6 | pyrrolidine | 0 | 55 | 1 | 22 | 1 | 38 |
| 5f | 6 | morpholine | −1 | 44 | 0 | 17 | 1 | 38 |
| 5g | 6 | piperazine | −3 | 14 | −1 | 0 | −1 | 20 |
| 5h | 6 | piperidine | −3 | 13 | −1 | 2 | −1 | 4 |
| 5i | 7 | pyrrolidine | 2 | 32 | 1 | 11 | 2 | 30 |
| 5j | 7 | morpholine | 1 | 25 | 0 | 10 | 2 | 32 |
| 5k | 7 | piperazine | 1 | 1 | 1 | 0 | 1 | 3 |
| 5l | 7 | piperidine | 1 | 29 | 1 | 8 | 2 | 25 |
| 8a | 6 | piperazine | −1 | 7 | 0 | 29 | −2 | 68 |

TABLE 2-continued

Antiproliferative of isoxazole derivatives.

| | | | Growth percentage | | | | |
|---|---|---|---|---|---|---|---|
| | | | MCF7 (Breast) | | NCI-H460 (Lung) | | SF-268 (CNS) | |
| Compd. | n | NR$_1$R$_2$ | 20 µg/mL | 4 µg/mL | 20 µg/mL | 4 µg/mL | 20 µg/mL | 4 µg/mL |
| 8b | 6 | 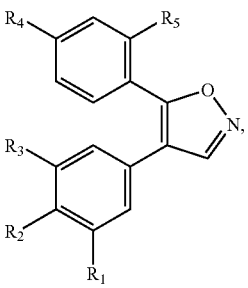 | 4 | 93 | 2 | 89 | 15 | 116 |

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An isoxazole derivative having the following formula:

wherein $R_1$, $R_2$, $R_3$, and $R_4$, independently, consist of hydrogen, hydroxy or $C_1$-$C_{12}$ alkoxy optionally substituted with oxirane, thiirane, aziridine, amino, cycloamino, aminohydroxy or cycloaminohydroxy; and $R_5$ consists of $C_1$-$C_{12}$ alkoxy optionally substituted with oxirane, thiirane, aziridine, amino, cycloamino, aminohydroxy or cycloaminohydroxy.

2. A pharmaceutical composition, comprising:

an isoxazole derivative as claimed in claim 1 or a pharmaceutically acceptable salt thereof; and a pharmaceutically acceptable carrier.

3. A pharmaceutical composition for treatment of osteoporosis, comprising:

an isoxazole derivative as claimed in claim 1 or a pharmaceutically acceptable salt thereof; and a pharmaceutically acceptable carrier.

4. A pharmaceutical composition for treatment of breast cancer, lung cancer and CNS cancer, comprising:

an isoxazole derivative as claimed in claim 1 or a pharmaceutically acceptable salt thereof; and a pharmaceutically acceptable carrier.

* * * * *